(12) United States Patent
Singh

(10) Patent No.: US 11,660,098 B2
(45) Date of Patent: *May 30, 2023

(54) HAND-HELD GRASPING DEVICE

(71) Applicant: City of Hope, Duarte, CA (US)

(72) Inventor: Gagandeep Singh, Duarte, CA (US)

(73) Assignee: City of Hope, Duarte, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 17/032,386

(22) Filed: Sep. 25, 2020

(65) Prior Publication Data

US 2021/0030422 A1 Feb. 4, 2021

Related U.S. Application Data

(63) Continuation of application No. 15/503,147, filed as application No. PCT/US2015/046048 on Aug. 20, 2015, now Pat. No. 11,172,935.

(60) Provisional application No. 62/067,782, filed on Oct. 23, 2014, provisional application No. 62/039,836, filed on Aug. 20, 2014.

(51) Int. Cl.
| | |
|---|---|
| *A61B 17/28* | (2006.01) |
| *A61B 17/122* | (2006.01) |
| *A61B 18/14* | (2006.01) |
| *A61B 17/062* | (2006.01) |
| *A61B 18/18* | (2006.01) |

(Continued)

(52) U.S. Cl.
CPC .......... *A61B 17/122* (2013.01); *A61B 17/062* (2013.01); *A61B 17/28* (2013.01); *A61B 18/1442* (2013.01); *A61B 17/2812* (2013.01); *A61B 17/3201* (2013.01); *A61B 18/1815* (2013.01); *A61B 2218/002* (2013.01); *A61B 2218/007* (2013.01); *B25B 7/10* (2013.01)

(58) Field of Classification Search
CPC . A61B 17/122; A61B 17/062; A61B 18/1442; A61B 17/2812; A61B 17/3201; A61B 18/1815; A61B 2218/002; A61B 2218/007; A61B 17/29; A61B 2018/145; A61B 2018/1462; B25B 7/10

See application file for complete search history.

(56) References Cited

U.S. PATENT DOCUMENTS

| | | |
|---|---|---|
| 640,517 A | 1/1900 | Acheson |
| 3,398,746 A | 8/1968 | Abramson |
| (Continued) | | |

OTHER PUBLICATIONS

Aesculap, Inc. (A B. Braun Company), Catalog—"Instruments and Devices for Bipolar Surgery," Sep. 2012. 35 pages.

(Continued)

*Primary Examiner* — Adam Z Minchella
(74) *Attorney, Agent, or Firm* — Mintz Levin Cohn Ferris Glovsky and Popeo, P.C.

(57) ABSTRACT

A hand tool has a pivot connection pivotally attaching a first arm to a second arm, with the pivot connection fixed relative to the first arm and movable to first and second positions relative to the second arm. A spring urges the pivot connection into the first position. When jaws on the front ends of the arms clamp tissue with force greater than a pre-set threshold, the spring force is overcome and the jaws may move linearly apart, allowing for more uniform clamping of the tissue. The first arm may have an arm spring extending between a front segment pivotally attached to a rear segment of the first arm.

13 Claims, 10 Drawing Sheets

(51) Int. Cl.
*A61B 17/3201* (2006.01)
*B25B 7/10* (2006.01)

(56) References Cited

U.S. PATENT DOCUMENTS

| | | | |
|---|---|---|---|
| 3,732,719 | A | 5/1973 | Pallotta |
| 4,241,861 | A | 12/1980 | Fleischer |
| 4,671,274 | A | 6/1987 | Sorochenko |
| 4,893,530 | A | 1/1990 | Warheit |
| 4,938,214 | A | 7/1990 | Specht et al. |
| 4,982,500 | A * | 1/1991 | Ramani ............ A61B 17/2812 30/261 |
| 5,019,092 | A * | 5/1991 | Klintmalm .......... A61B 17/122 81/418 |
| 5,116,332 | A | 5/1992 | Lottick |
| 5,300,087 | A * | 4/1994 | Knoepfler ............ A61B 17/29 604/35 |
| 5,395,312 | A | 3/1995 | Desai |
| 6,010,516 | A | 1/2000 | Hulka |
| 6,679,881 | B1 | 1/2004 | Bybee |
| 6,863,669 | B2 | 3/2005 | Spitzer |
| 7,422,591 | B2 | 9/2008 | Phan |
| 7,842,045 | B2 | 11/2010 | Vandenbroek |
| 9,173,707 | B2 | 11/2015 | Singh |
| 9,186,214 | B2 | 11/2015 | Singh |
| 9,186,215 | B2 | 11/2015 | Singh |
| 9,480,526 | B2 | 11/2016 | Singh |
| 9,492,222 | B2 | 11/2016 | Singh |
| 9,629,676 | B2 | 4/2017 | Singh |
| 9,848,942 | B2 | 12/2017 | Singh |
| 9,872,730 | B2 | 1/2018 | Singh |
| 11,172,935 | B2 * | 11/2021 | Wong ................. A61B 17/122 |
| 2002/0016591 | A1 | 2/2002 | Levine et al. |
| 2003/0018331 | A1 | 1/2003 | Dycus et al. |
| 2003/0181910 | A1 | 9/2003 | Dycus et al. |
| 2005/0159745 | A1 | 7/2005 | Truckai et al. |
| 2005/0203499 | A1 * | 9/2005 | Pendekanti ............. A61N 7/02 606/27 |
| 2006/0235379 | A1 | 10/2006 | McClurken et al. |
| 2007/0049920 | A1 | 3/2007 | McClurken et al. |
| 2009/0163905 | A1 | 6/2009 | Winkler et al. |
| 2010/0185232 | A1 * | 7/2010 | Hughett, Sr. ...... A61B 18/1445 606/205 |
| 2010/0292691 | A1 | 11/2010 | Brogna |
| 2011/0004208 | A1 | 1/2011 | Truckai et al. |
| 2012/0022584 | A1 * | 1/2012 | Donnigan ............. A61B 17/29 606/206 |
| 2012/0111157 | A1 * | 5/2012 | Qiu ........................ B25B 7/10 81/409 |
| 2012/0209263 | A1 | 8/2012 | Sharp et al. |
| 2013/0018411 | A1 | 1/2013 | Collings et al. |
| 2013/0218159 | A1 | 8/2013 | Kappel et al. |
| 2013/0296843 | A1 | 11/2013 | Boudreaux et al. |
| 2014/0088582 | A1 | 3/2014 | Singh |
| 2014/0298661 | A1 | 10/2014 | Carmichael et al. |
| 2015/0148834 | A1 | 5/2015 | Gee et al. |
| 2015/0282865 | A1 | 10/2015 | Tetzlaff et al. |
| 2016/0317216 | A1 | 11/2016 | Hermes et al. |
| 2017/0224348 | A1 | 8/2017 | Wong et al. |
| 2018/0185086 | A1 | 7/2018 | Singh |
| 2018/0206917 | A1 | 7/2018 | Singh |

OTHER PUBLICATIONS

Aragon Surgical, Inc., "CAIMAN breeds confidence", Lektrafuse CAIMAN product brochure, 3 pages (Jan. 2010).

* cited by examiner

HAND-HELD GRASPING DEVICE

CROSS-REFERENCES TO RELATED APPLICATIONS

This application is a Continuation of U.S. application Ser. No. 15/503,147, filed Feb. 10, 2017, which is a § 371 and claims priority of PCT/US2015/46048 filed Aug. 20, 2015, and claims priority to the following U.S. patent applications: (1) U.S. Provisional Patent Application No. 62/039,836, entitled "Parallel Sustained Pressure Hinge/Parallel Jaw Apposition Clamp" and filed Aug. 20, 2014; and (2) U.S. Provisional Patent Application No. 62/067,782, entitled "Hand tool" and filed Oct. 23, 2014. The entire contents of the aforementioned patent applications are incorporated herein by their entirety.

BACKGROUND

The present disclosure relates to a hand-held tool for gripping and/or compressing an object.

Various designs of plyers-type hand-tools have been proposed for specific applications. Generally these tools have two pivotally attached arms with the arms acting as levers to increase the gripping or compression force applied by jaws at the front end of the arms. In the medical and surgical field, hemostats and surgical clamps are examples of these types of tools.

One specific, non-limiting example in the surgical field is removal of part of the liver (hepatic resection), which is often performed to remove a tumor. Blood loss is a serious complication associated with this procedure. Multiple surgical techniques and devices have been developed to minimize blood loss and improve outcomes in hepatic resection. The so-called clamp-crush technique is a preferred technique.

The clamp-crush technique generally involves crushing the liver parenchyma using a hemostatic clamp tool to expose small vessels and biliary radicals, which are then divided and sealed via radio frequency (RF) energy provided to the jaws of the tool. Various tools have been proposed for this purpose. However, challenges remain in providing a coaptive surgical sealing tool offering superior performance and efficiency in a simple and low-cost design.

SUMMARY

A hand tool has a pivot connection pivotally attaching a first arm to a second arm, with the pivot connection fixed relative to the first arm and movable to first and second positions relative to the second arm. A jaw spring urges the pivot connection into the first position. When jaws on the front ends of the arms clamp with force greater than a pre-set threshold, the spring force of the jaw spring is overcome and the jaws may move linearly apart, allowing for more uniform clamping. An arm spring in the first arm may limit the clamping force that may be applied to the clamped object.

In one aspect, there is disclosed A hand-held tool comprising: a first arm having a first jaw section and a first handle section; a second arm having a second jaw section and a second handle section; a pivot connection pivotally attaching the first arm to the second arm, wherein the pivot connection is fixed relative to the first arm and movable between first and second positions relative to the second arm; and a jaw spring urging the pivot connection into the first position.

In another aspect, there is disclosed A hand tool comprising: a first arm having a front section pivotally attached to a rear section via an arm hinge pin; an arm spring extending between the front section and to the rear section of the first arm; a jaw hinge pin pivotally connecting the front section of the first arm to a second arm, with the hinge pin at a fixed position on the first arm, and the hinge pin movable into first and second positions relative to the second arm; and a jaw spring urging the hinge pin towards the first position, and wherein the hinge pin is movable against the bias of the spring into the second position, wherein the front sections of the first and second arms may be spaced apart and substantially parallel to each other.

In another aspect, there is disclosed a hand tool comprising: a first arm having a front section pivotally attached to a rear section via an arm hinge pin; an arm spring extending between the front section and to the rear section of the first arm; a jaw hinge pin pivotally connecting the front section of the first arm to a second arm, wherein the hinge pin is at a fixed position on the first arm, and the hinge pin is movable into first and second positions relative to the second arm; a jaw spring urging the hinge pin towards the first position, and with the hinge pin movable against the bias of the spring into the second position wherein front sections of the first and second arms may be spaced apart and substantially parallel to each other; a first electrode on the front section of the first arm, and a second electrode on a front section of the second arm; wire leads on at least one of the first and second arms connecting to the first and second electrodes; and an irrigation line in or on at least one of the first and second arms connecting to front section of the first or second arms, and an aspiration line in or on at least one of the first and second arms connecting to the front section of the first or second arms.

Other features and advantages should be apparent from the following description of various embodiments, which illustrate, by way of example, the principles of the disclosure.

BRIEF DESCRIPTION OF THE DRAWINGS

In the drawings, the same element number indicates the same element in each of the views.

DETAILED DESCRIPTION

Disclosed is a hand tool for uses such as, for example, general manufacturing, assembly, and repair where grasping, clamping and/or holding is needed. The tool is sometimes described herein in the context of being a coaptive surgical sealing tool although it should be appreciated that this is just an example and that the tool is configured for use in a variety of situations.

Figure 1:
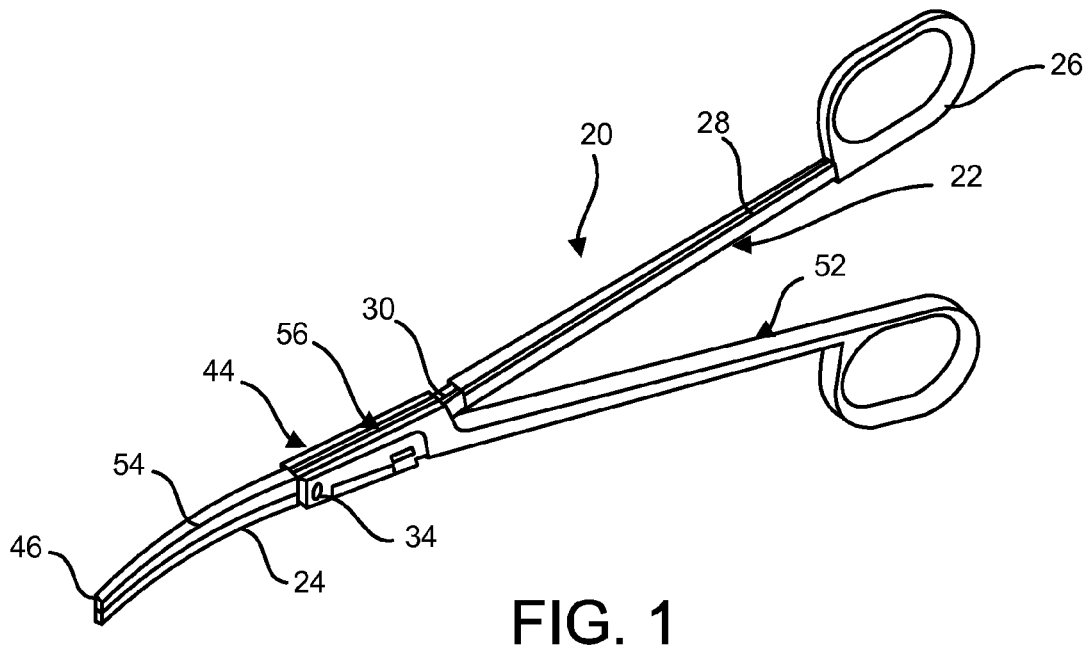
FIG. 1 is a front, top and side perspective view of a hand tool.
Figure 2:
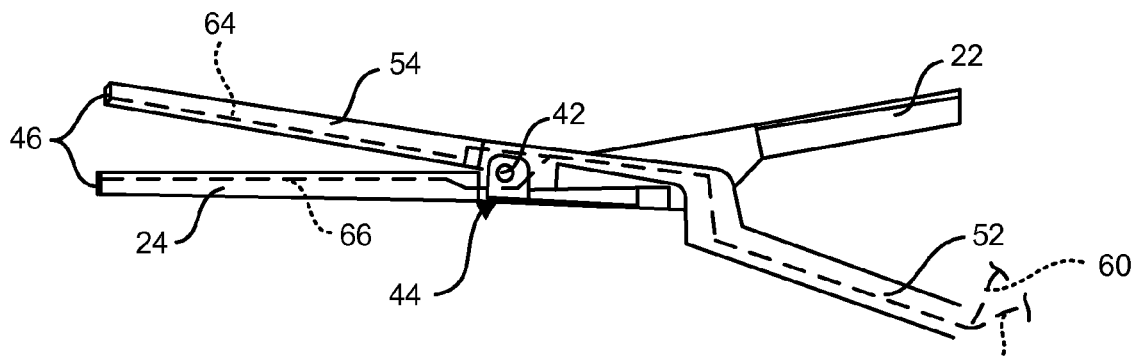
FIG. 2 is a side view of the tool shown in FIG. 1.
Figure 3:
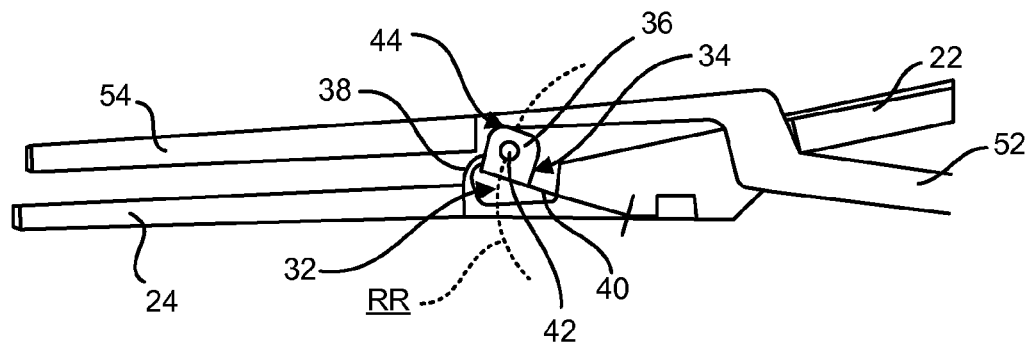
FIG. 3 is an enlarged detail view of the tool of FIG. 1.

As shown in FIGS. 1-3, a first embodiment of a hand tool 20 has a first arm 22 pivotally attached to a second arm 52 at a hinge joint 44. The front section (forward of the hinge joint 44) of the first arm 22 has a first jaw 24 and the front section of the second arm 52 similarly has a second jaw 54. A grabbing element, such as a finger ring 26, is provided at the back end of the back section 28 of each of the arms 22 and 52. The second arm 52 includes an arm slot or opening 56, with a reduced width hinge section 30 of the first arm 22 positioned within the slot 56. Referring to FIG. 2, where the tool 20 is configured as a surgical tool, wire leads 60 and 62 may optionally be provided on or in one or both arms 22 and 52 to electrodes 66 and 64 on the arms 22 and 52. The wire leads 60 and 62 may terminate at a connector on one or both of the arms, to allow energy such as RF (radio frequency) or microwave energy, to be supplied to the electrodes. In an embodiment the energy is at a frequency of at least 100 kHz. In another embodiment, microwave frequency is greater than 300 mHz.

As shown in FIG. 1, for applications such as surgery of the liver, the jaws 24 and 54 may be made long and slender, for example with a length from the hinge joint 44 to the front tip 46 of each jaw ranging from about 20 to 80 mm, or 30-40 mm, and with jaws having a maximum width and maximum height of about 1.5 to 5 mm. The jaws may taper outwardly in height and width from the front tip to the hinge joint 44, with the width and height of each jaw 1 to 2.5 times greater at the hinge joint 44 than at the front tip 46. The jaws 24 and 54 may also curve to one side, such as the left side in the example shown in FIG. 1. It should be appreciated that the aforementioned dimensions are just examples and that variations are within the scope of this disclosure.

Turning to FIG. 3, a spring arm 40 of a spring 34 may be attached to the first arm 22. The spring 34 may have spaced apart upright clevis plates 36 on opposite sides of the second arm 52, with a hinge pin 42 extending through the plates 36 and the second arm 52 to form the hinge joint 44. The hinge pin 42 is movable via flexing of the spring 34, from an up or open position shown in FIG. 3, to a down or closed position shown in FIG. 2. In the up position the hinge pin 42 is raised up and largely out of a recess 32 in the first arm 22 as shown in FIG. 3. In the down position the hinge pin 42 is largely within the recess 32 as shown in FIG. 2. As shown in FIG. 2, in the down position, the plane or axis of each jaw may be centrally aligned with the hinge pin 42, with the jaws parallel to and in contact with each other. The hinge pin 42 defines an axis of rotation of the first arm 22 and the second arm 52 relative to one another wherein the axis of rotation can change position based on the position of the spring arm 40.

Referring to FIG. 2, in use the jaws 24 and 54 are opened, moved to engage an object, such as a work piece, or tissue, and then closed. With nominal clamping pressure applied, in a surgical application the jaws may act as conventional hemostat or clamping jaws, as shown in FIG. 2. However, if greater clamping pressure is applied, the force acting to separate the jaws exceeds the force of the spring acting to hold the hinge pin 42 in the down position. As this occurs, the hinge pin 42 moves up (or away from the first arm 22) towards the up position shown in FIG. 3. Correspondingly, the jaws move linearly away from each other rather than to the teen relative to one another. As a result, the jaws are able to clamp the work piece, or tissue, with more uniform clamping force. The linear separating movement of the jaws may be limited by a finger 38 on the first arm providing a hard stop position against the spring 34. The linear separating movement of the jaws depends on the reaction force on the jaws (acting to separate the jaws). Depending on the geometry of the clamped object or tissue, the linear separating movement may be independent of the pivoting movement or angular position of the jaws.

With the jaws closing at an acute angle as shown in FIG. 2, the clamping force is greater closer to the hinge joint 44 and less at the tip 46, so that the clamping force may vary significantly. With the tool 20, however, after a pre-set clamping force is exceeded, the jaws move apart linearly, helping to provide a more uniform clamping force. As shown in FIG. 3, the jaws may remain substantially parallel as they move linearly apart. The pre-set clamping force is selected via the spring constant of the spring. Different embodiments of the tool 20 may have springs with different spring constants selected for use in different hand tool uses, or different surgical procedures. For a non-limiting example, the spring constant may be in the range of 2-8 Newtons/meter or 36 Newtons/meter.

In the configuration shown in FIGS. 1-3, the hinge pin 42 moves in an arc having a radius equal to the length of the spring arm 40. Consequently, as the jaws move linearly relative each other, there is also a small front/back movement as well. Hence, with the jaws fully linearly open, and the hinge pin 42 in the full up position, the second jaw is positioned slightly behind the first jaw 22, as shown in FIG. 3. Clearance to allow for this slight longitudinal shifting between the jaws may be provided via the leg slot 56. The hinge pin 42 vertical range of travel may be about 2-10 or 3-7 mm.

Figure 4:
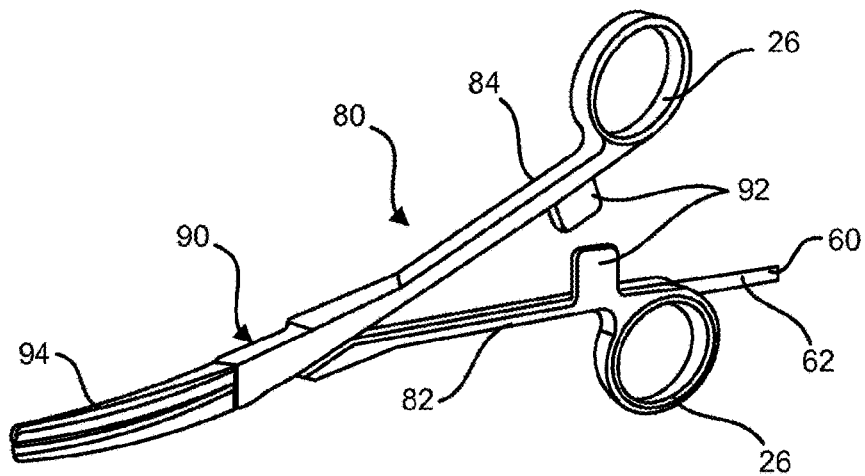
FIG. 4 is a front, top and side perspective view of a second embodiment of a hand tool.
Figure 5:
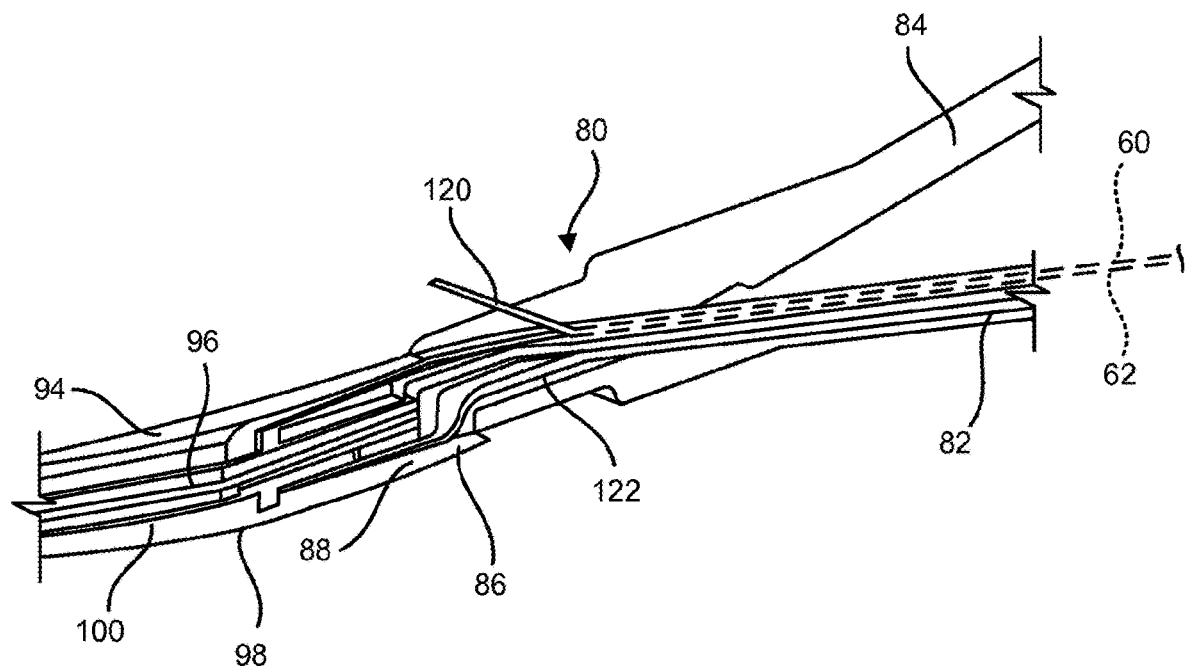
FIG. 5 is an enlarged section view detail of the tool of FIG. 4.
Figure 6:
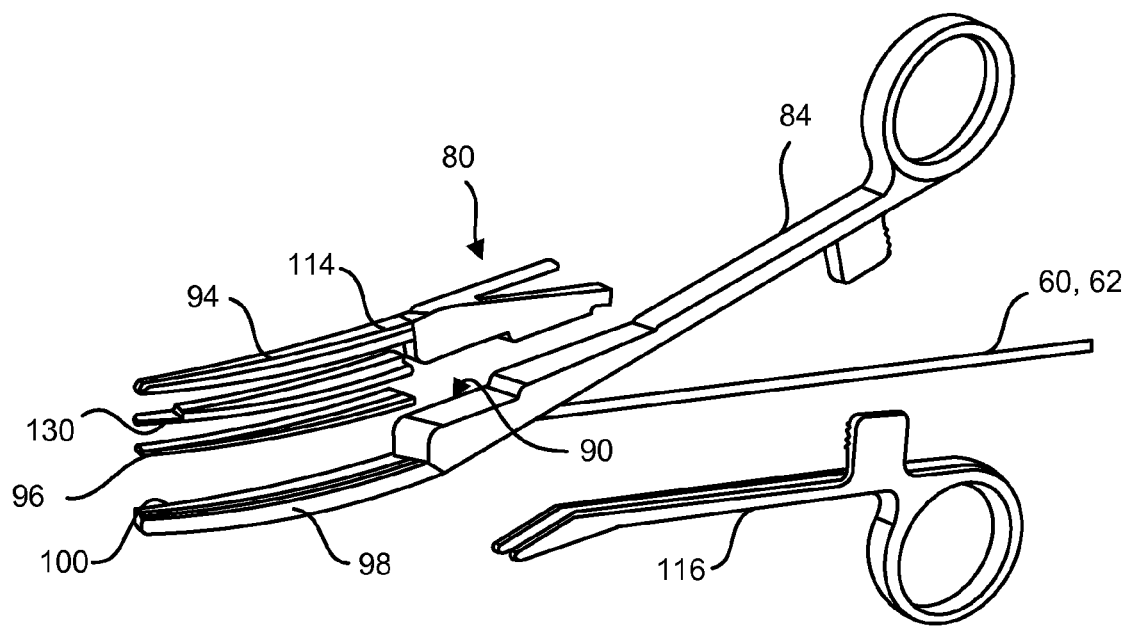
FIG. 6 is an exploded perspective view of the tool of FIG. 4.

Turning to FIGS. 4-6, in a second embodiment 80, a first arm 82 is pivotally attached to a second arm 84 via a hinge pin 86. Latch plates 92 may be used to latch the arms. As shown in FIG. 5, as applied to a surgical hand tool, electrical leads 60 and 62 along with an irrigation line or drip 120 and an aspiration or suction line or tube 122 may extend on or in either arm to electrodes 96 and 100 on first and second arms 94 and 98. The tubes or lines 120 and/or 122 may be routed in a joggle around the hinge pin 86. As shown in FIG. 6, the first arm 82 may be provided with separate front and back sections 114 and 116, such as to allow for easier manufacture. The first arm 82 may be positioned within an arm slot 90 of the second arm 84. Also as shown in FIG. 6, an insulator plate or layer 130 may be positioned between the arms 94 and 98 and the electrodes 96 and 100. Irrigation and aspiration lines may also be provided on the tool 20.

Figure 7:
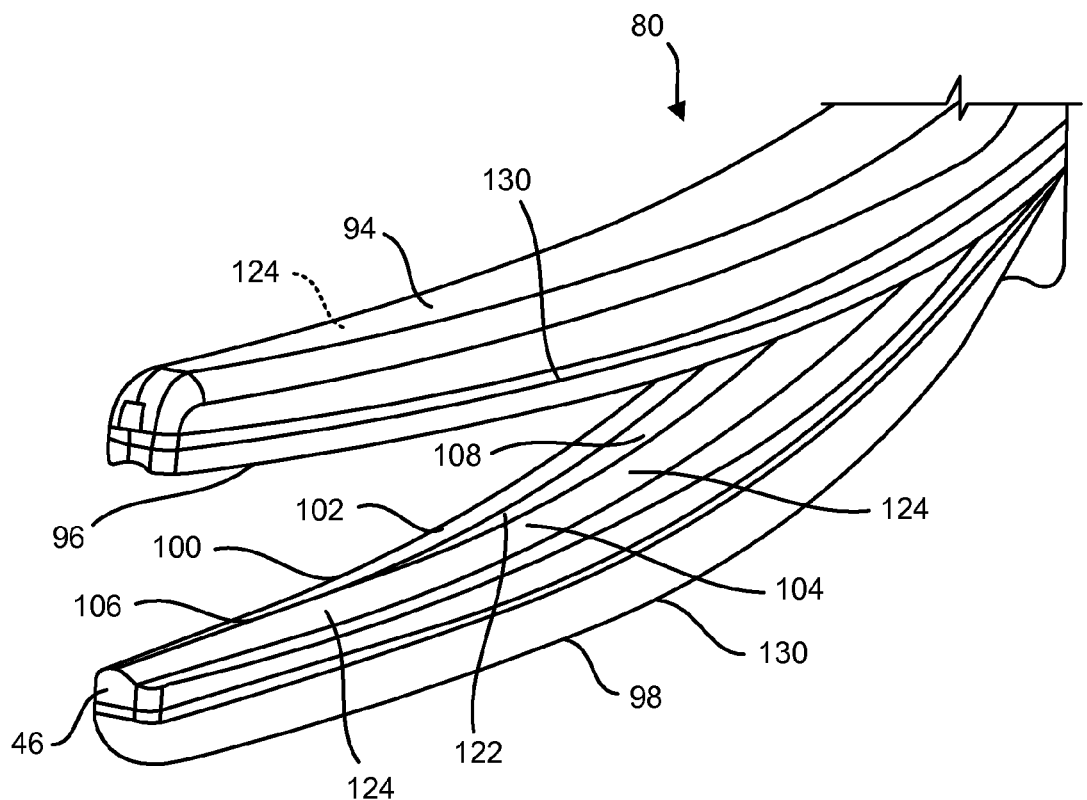
FIG. 7 is an enlarged perspective view of the jaws of the tool of FIG. 4 in an open angle position.

As shown in FIG. 7, the electrodes 96 and 100 may have angled complimentary surfaces 102 and 104 joining together at an edge 106 adjacent to the tip 46. Aspiration and irrigation openings 124 and 126 connecting with the aspiration and irrigation lines may be provided in the electrodes 96 and 100. As shown in dotted lines in FIG. 7, the aspiration openings 124, if used, may also be located on a top and/or side surface of one or both jaws, in addition to, or instead of, locating the aspiration openings in the electrodes. The electrodes 96 and 100 may have complimentary shapes, so that the jaws mate uniformly when closed, with little or no space between them. The inner surfaces of one or more of the arms may be textured or can have any surface characteristic, such as serrations, that improves the gripping ability of the arms relative to tissue or other material. The serrations, if present, may also be shaped to bias any irrigation to flow toward a predetermined location of the arms, such as toward a front region.fparalle In another embodiment, one or both arms may have a portion that is flexible or movable relative to another portion of the arm. For example, a tip region of one or both of the arms may pivot or rotate relative to a second region of the arm. The rotatable or pivotable portion may be spring-loaded toward a default position.

Figure 8:
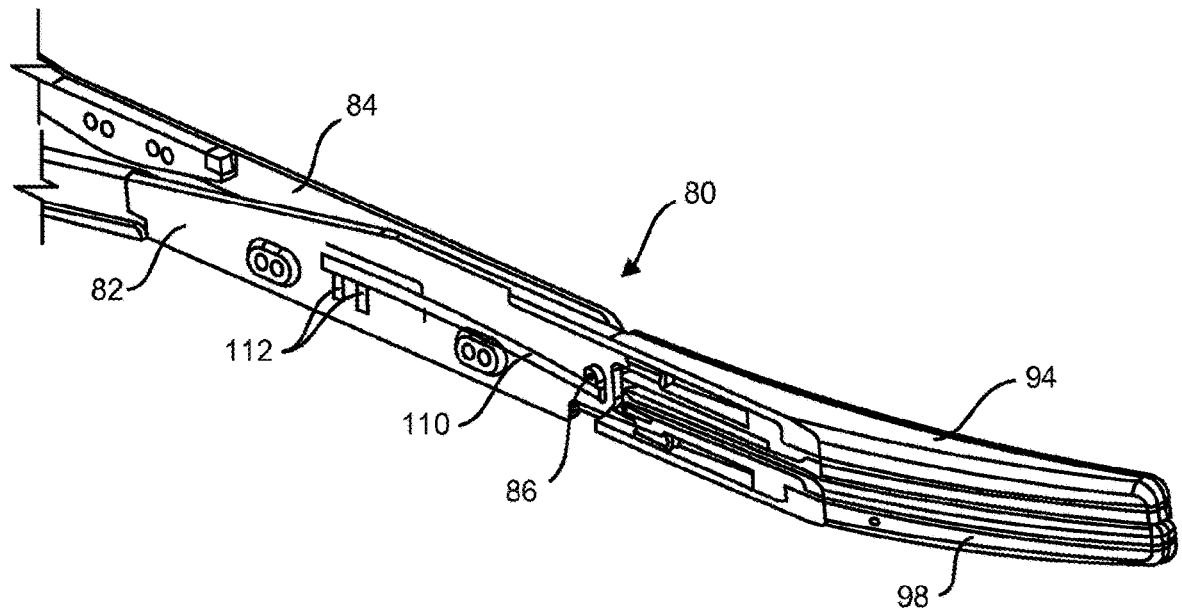
FIG. 8 is a side view of the tool of FIG. 4 in the closed position.
Figure 9:
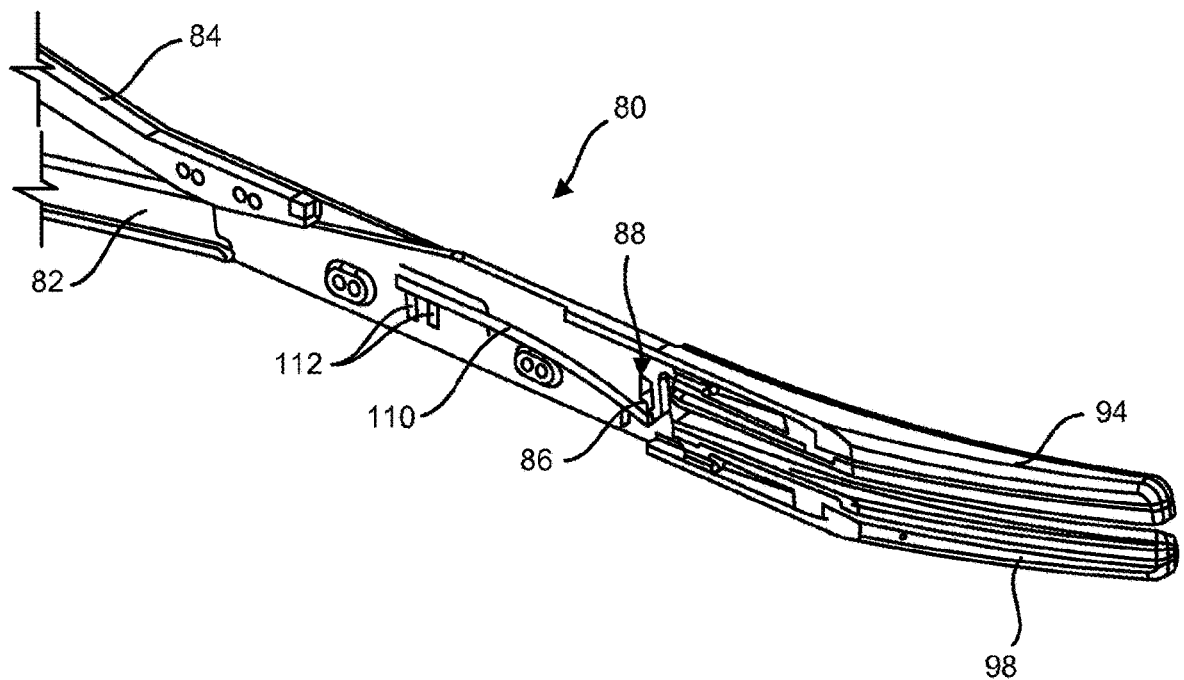
FIG. 9 is a side view of the tool of FIG. 4 in the open parallel position.

Turning to FIGS. 8 and 9, the hinge pin 86 on the second arm 84 may extend into a pin slot 88 in the first arm 82. A jaw spring 110 may be attached to the first arm 82 with set screws 112. The jaw spring 110 exerts upward force on the hinge pin 86, holding the jaws together, as shown in FIG. 8.

Referring to FIG. 9, as with the tool 20, when the jaws clamp onto an object with a force exceeding a pre-set amount, the force of the jaw spring 110 is overcome. The hinge pin 86 moves from the up position shown in FIG. 8, to the down position shown in FIG. 9, where the jaws are spaced apart and may be largely parallel to each other. The jaw spring 110 may be a spring wire. Other forms of springs such as coil compression springs, leaf springs and non-metal spring elements, such as resilient foam, rubber and plastic elements, may also be used.

As described, the pivot pin 42 or 86 provides a pivot point where the arms intersect, with the pivot point moving along a linear or curvilinear pathway up or down to accommodate the thickness of the clamped object. The spring moves the pivot pin. If the spring constant is too high, the pivot point will not move enough to keep the jaws parallel. Similarly, if the spring constant is too low, the spring will allow the pivot pin to move too easily, with the pivot pin moving too far to keep the jaws parallel. The spring constant may be selected based on the characteristics of the object to be clamped, or in surgical applications, the stiffness of the tissue to be operated on.

Relative to surgical uses, testing on calf liver revealed that 5 N of force was sufficient to fully collapse the calf liver, suggesting that a spring force on the order of 5 N may be suitable in some embodiments of the tool 20. As shown in FIGS. 8 and 9, securing the jaw spring 110 in place with fasteners 112 allows the spring to be quickly and easily replaced. This allows the tool 80 to be adapted for different uses.

In addition to providing more even and uniform clamping force along the long jaws, the capability of providing parallel jaws, in surgical applications, also promotes an even seal along the long jaws. Substantially parallel jaws also tends to obviate any need for segmented RF tips on the jaws to allow different power or time settings along the jaw's length, and the associated added RF generator complexity and lead wires. In an embodiment, the jaws initially pivot or rotate relative to one another when initially opened and then transfer to parallel position and translate relative to one another without any pivoting after the arms have initially achieved a certain level of movement relative to one another.

Figure 10:
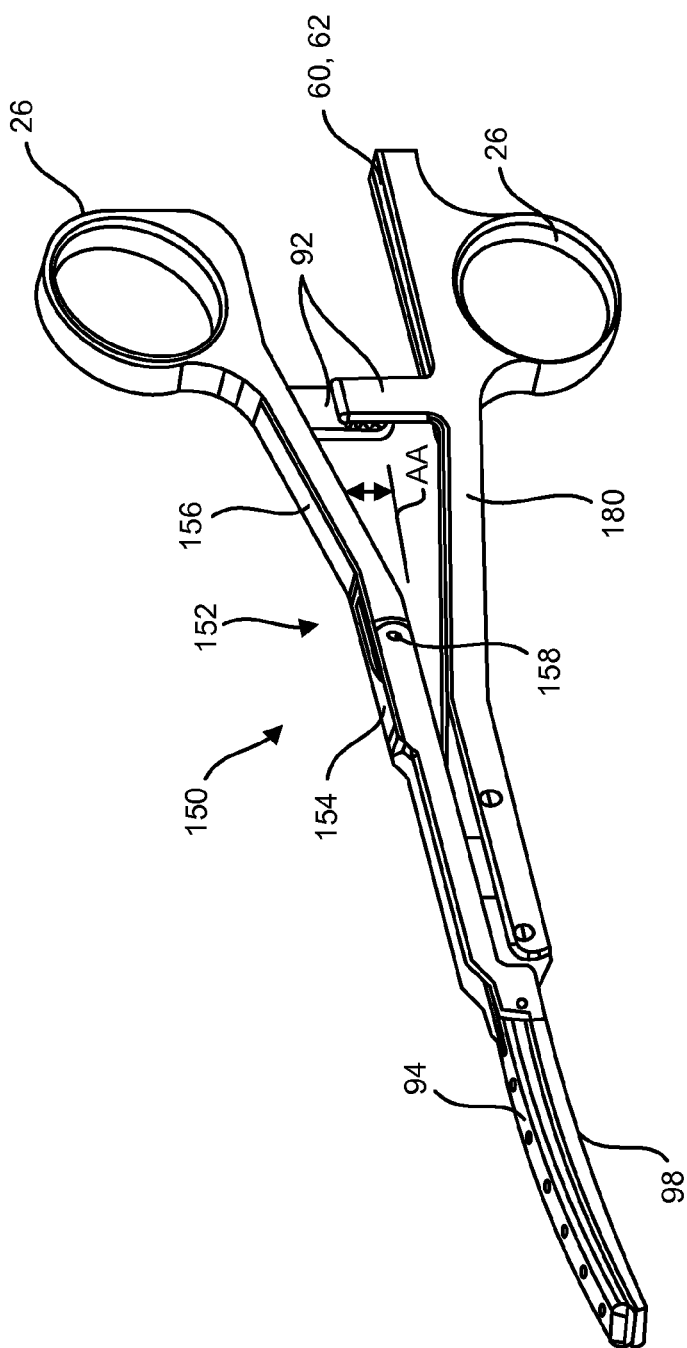
FIG. 10 is a front, top and side perspective view of another embodiment of a hand tool.
Figure 11:
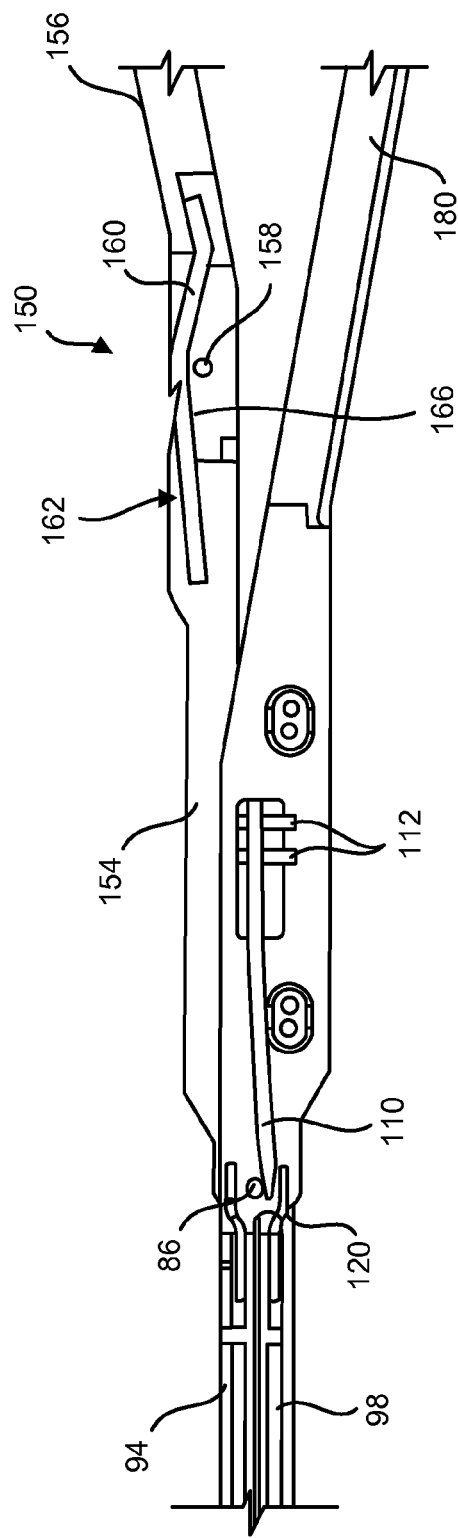
FIG. 11 is a side view of the tool shown in FIG. 10.
Figure 12:
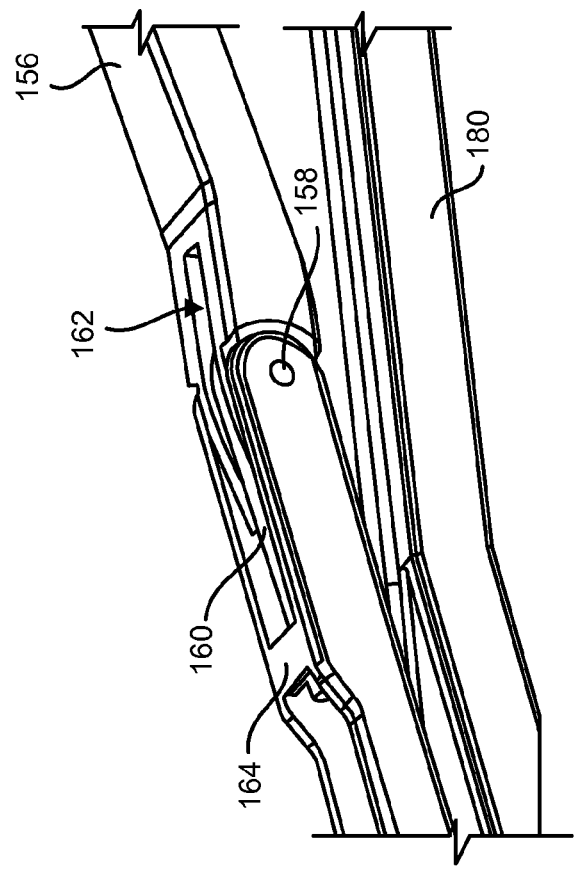
FIG. 12 is an enlarged top, front and side perspective view of the first arm of the tool shown in FIGS. 11 and 12.

Turning to FIGS. 10-12, a third hand tool 150 may be the same as the second tool configuration 80 shown in FIGS. 4-9, with the following changes. A first arm 152 is divided into a front segment 154 pivotally attached to a rear segment 156 via an arm hinge pin 158. As shown in FIGS. 11 and 12, an arm spring 160 extends between the front segment 154 and the rear segment 156. The arm spring 160 may be provided in the form of a spring wire, or as another type of spring similar to the alternative spring options discussed above for the jaw spring 110. The arm spring 160 may be positioned within a spring slot 162 in the top surface of the front and rear segments.

As shown in FIG. 11, the central section of the arm spring 160 may be supported on a curved arch surface 166 extending over the hinge pin 158, to reduce bending stresses on the arm spring 160. The ends of the arm spring 160 may be positively attached to the front and rear segments via set screws, bonding, welding, etc. Alternatively, as shown in FIGS. 11 and 12, the arm spring 160 may be held in place via spring force, with the front end of the arm spring 160 captured under a bridge section 164 on the front segment, as shown in FIG. 12, and with the back end of the arm spring 160 captive within a slot in the rear segment 156, as shown in FIG. 11. Capturing the arm spring 160, rather than positively attaching the arm spring 160 to the segments allows the arm spring 160 to move slightly relative to the arm segments when the rear segment pivots relative to the front segment, which may simplify the hinge design.

An embodiment of arm spring 160 resists any deflection until the desired compression force limit is reached, so that the tool 150 would have a familiar feel and operation in the surgeon's hand. Such man arm spring 160 also then freely allows deflection when the desired compression force is exceeded, to as to precisely limit the compression force. Alternative spring configurations may be used to simulate such a spring. For example, laterally curved leaf springs, collapsing hollow tube springs, and similar alternatives may be used in place of a solid round wire to better achieve preferred handling characteristics of the tool 150.

The arm spring 160 is pre-loaded or tensioned so that it exerts torque acting counterclockwise about the arm hinge pin 158 in FIG. 11. Consequently, the arm spring 160 holds the rear segment 156 in a straight or locked out position as shown in FIGS. 11 and 12. In ordinary use with nominal clamping force applied, the tool 150 operates in the same way as the tool 80 shown in FIGS. 4-6. However, if excessive force is applied, the arm spring 160 will bend, allowing the rear segment 156 of the first arm 152 to pivot about the arm hinge pin 158 downward towards the second arm 180. Consequently, the clamping force applied by the jaws is automatically limited. As a result, inadvertent crushing of the clamped object is avoided. Damage to the long slender jaws caused by inadvertently clamping down on a hard object is also avoided. The arm spring 160 may be selected to have a spring constant which limits the clamping force to a desired maximum, for example 3-5 Newtons.

Referring back to FIGS. 10 and 11 the rear arm segment 154 may have an upward curve, or an upward angle AA of 10-35 degrees, to provide clearance for pivoting movement of the rear arm segment when the compression force limit is exceeded. The second arm 180 may also curve away or extend at angle away from the first arm 150 for the same purpose. The pivoting design of the first arm 152 may optionally be used on the second arm 180, or on both arms.

Also as shown in FIGS. 10 and 11, the arm hinge pin 158 may generally be located at a midpoint between the handle loop 26 and the jaw hinge pin 86. Of course, the specific position of the arm hinge pin 158 may be shifted to the front or back of the first arm, depending on the tool application.

Figure 13:
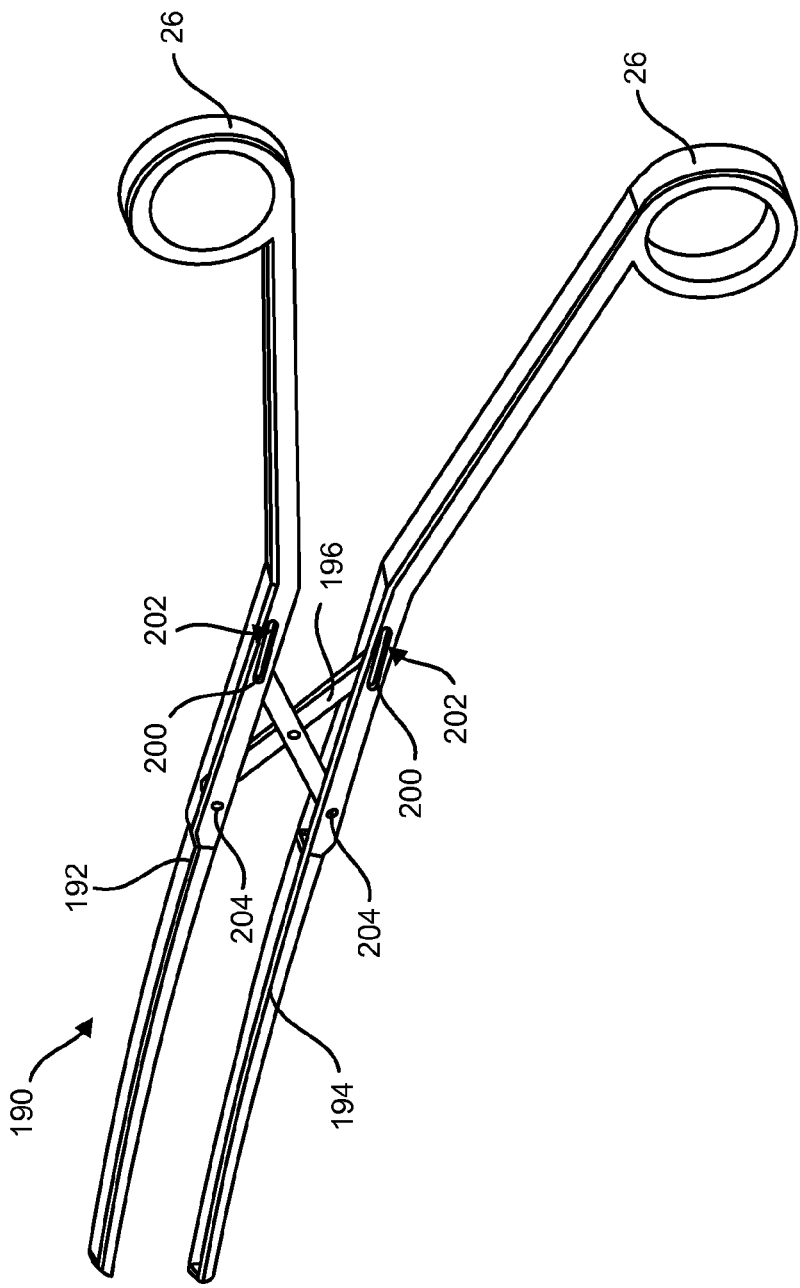
FIG. 13 is a front, top and side perspective view of another embodiment of a hand tool.

FIG. 13 shows a fourth tool embodiment 190 having a first arm 192 and a second arm 194 which may be a mirror image of the first arm 192. The arms 192 and 194 are connected by an X-linkage 196. The front ends of the X-linkage may be pivotally pinned to the arms via front pins 204, and the back ends of the X-linkage having slide pins 200 in slots 202. The X-linkage 196 keeps the arms parallel, as the arms opened and closed.

Figure 14:
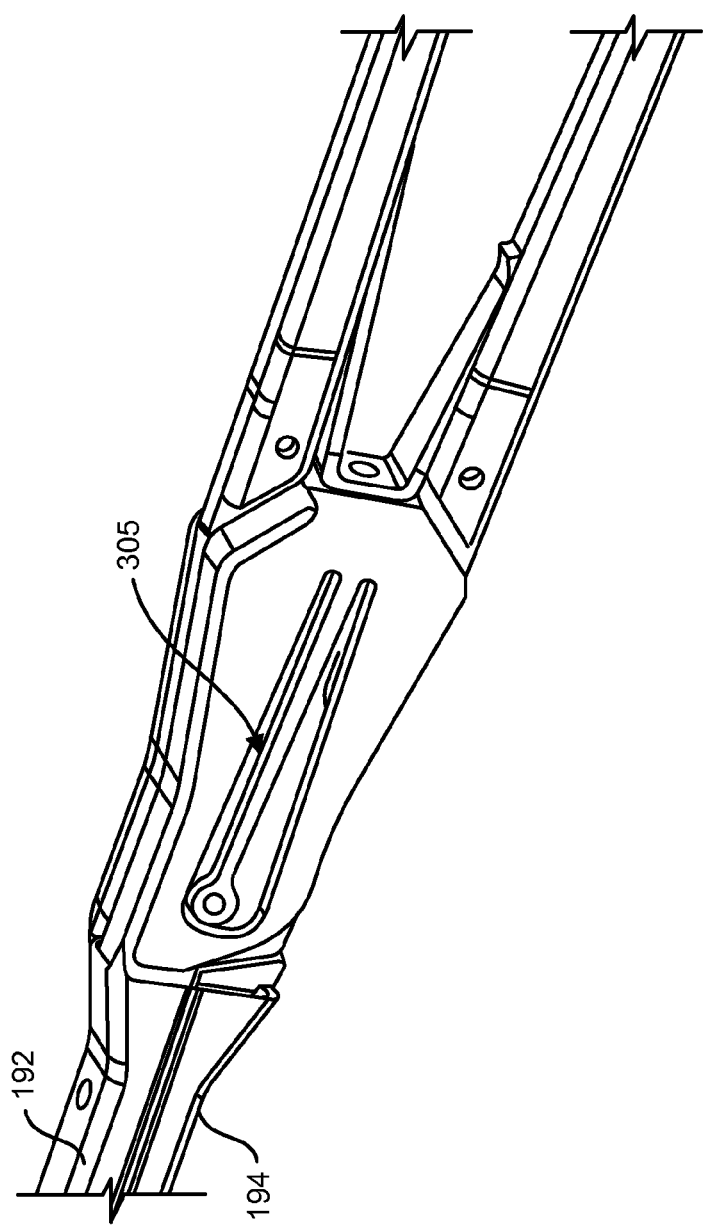
FIG. 14 shows another embodiment of a hand tool.

FIG. 14 shows a portion of the tool embodiment at the juncture between the handle portion 300 and the arms 192 and 194. A flexure element formed of an elongated, cantilevered arm 305 is positioned at the juncture in a manner that interacts with the arms 192 and 294 in a manner that maintains the arms in a parallel position when the arms are clamping something, such as when clamping tissue. The arm 305 is mechanically coupled to a structure positioned between the arms of the handle portion 300.

Figure 16:
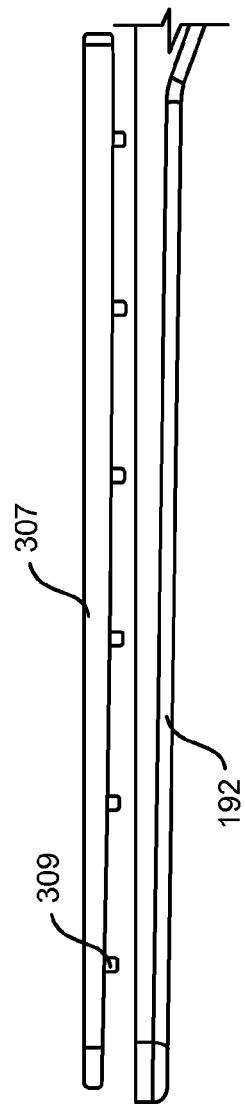
FIG. 16 shows a side view of the arm of FIG. 15.
Figure 15:
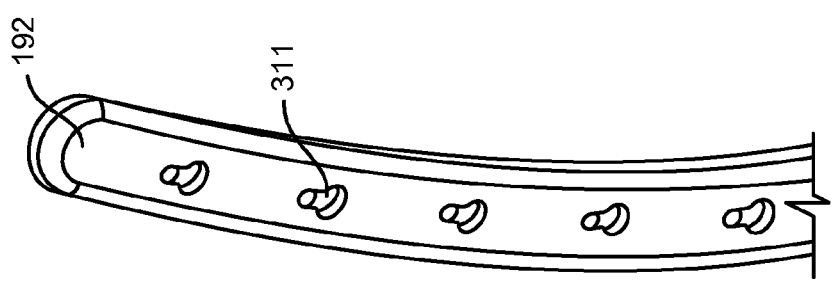
FIG. 15 shows a perspective, enlarged portion an arm of the tool.

FIG. 15 shows a perspective, enlarged portion of one of the arms 192. FIG. 16 shows a side view of the arm 192. An electrode 307 removably attaches to the arm 192 along the length of the arm 192. In an example embodiment, the electrode 307 includes one or more protrusions 309 that lockingly mate with complementary key-shaped openings 311 of the arm 192. For example, the protrusions 309 can mate with the openings 311 in a slide and lock manner such that the protrusions are inserted into the openings 311 and then are slide along a key-shaped portion of the openings to lock therein. In another embodiment, the protrusions snap into and lockingly engage with the openings such as in a press fit manner. Other mechanisms for coupling and locking the electrode to the arms are within the scope of this disclosure. For example, the electrode may slide onto the arm such as in a front-loading manner such that the electrode slides into or onto the arm from the front of the device. In another embodiment, the protrusions are on the arm and the openings are on the electrode. A similar arrangement can be used for the other arm 194.

Figure 17:
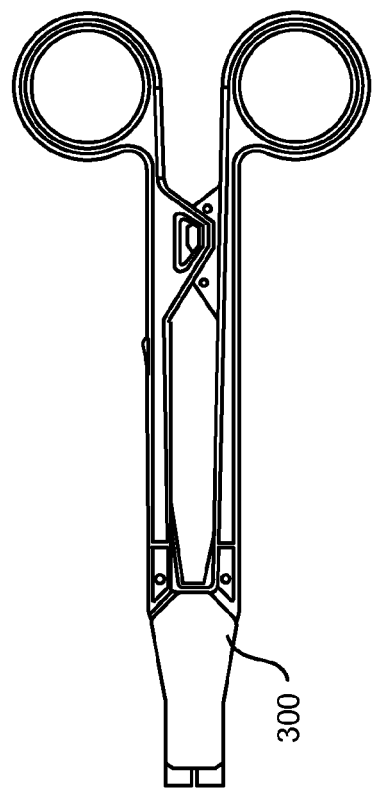
FIG. 17 shows another embodiment of a hand tool.
Figure 17:
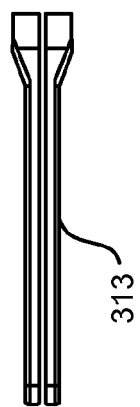

In an embodiment, at least a portion of the device is disposable and another portion of the device is reusable. For example, as shown in the embodiment of FIG. 17, the tool includes a disposable pair of removable arms or jaws 313 that removably mate with a handle portion 300 that is reusable. The arms 313 can removably mate with or otherwise removably couple to the handle portion 300. This can occur using any of a variety of mechanisms, such as in a sliding tongue and groove mechanism wherein the arms slidingly engage and lock with the handle portion 300.

As used here, unless otherwise stated, "in contact with" means elements actually or nominally touching each other, such as elements 1 or 2 mm apart. The term "linearly" is used here to distinguish from pivotal movement, and does not connote any geometrically precise linear characteristic. The term "joined", "attached" or "connected to" means temporarily or permanently physically linked with, or integral with, as with different sections of a single integral element.

The elements described above may of course also be applied in other products having similar elements, movements or requirements. These include, for example door hinges, to create a weather tight seal, or as a hinge on a trunk or case, or a briefcase allowing for expansion when filled over capacity. The elements and principles described may also be applied to a gas or fluid tank cap to regulate or relieve pressure, or as a pouch sealer to equalize pressure on the seal.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A hand-held, operating tool comprising:
a first arm having a first jaw section and a first handle section, the first jaw section having a first clamp surface;
a second arm having a second jaw section and a second handle section, the second jaw section having a second clamp surface;
a single pivot connection pivotally attaching the first arm to the second arm, wherein the pivot connection is fixed relative to the first arm and movable between a first position relative to the first arm and a second position relative to the second arm, and wherein the first clamp surface and the second clamp surface are non-parallel when the pivot connection is in the first position, and wherein the first clamp surface and the second clamp surface are parallel when the pivot connection is in the second position; and
wherein the pivot connection automatically moves to the second position when the first jaw section and the second jaw section clamp onto an object with a force exceeding a pre-set force amount such that the first jaw section linearly translates relative to the second jaw section without pivoting.

2. The operating tool of claim 1, further comprising a jaw spring that biases the pivot connection into the first position.

3. The operating tool of claim 2, wherein the pre-set force amount relates to a spring force of the jaw spring.

4. The operating tool of claim 2, wherein the spring comprises a wire spring attached to the second arm.

5. The operating tool of claim 1, wherein the pivot connection comprises a hinge pin fixed to the first arm and extending into a slot in the second arm.

6. The operating tool of claim 1, wherein the first jaw section is spaced apart from and substantially parallel to the second jaw section when the pivot connection is in the second position.

7. The operating tool of claim 1, wherein the first jaw section and the second jaw section each have a front end and a back end, and wherein the front and back ends of the first and second jaw sections are spaced apart from each other, respectively, when the pivot connection is in the second position.

8. The operating tool of claim 7, wherein the spacing between the front and back ends of the first and second jaw sections varies by less than 2 mm when the pivot connection is in the second position.

9. The operating tool of claim 1, further comprising a first electrode on the first jaw section and a second electrode on the second jaw section, and wire leads on at least one of the first and second arms connecting to the first and second electrodes.

10. The operating tool of claim 9, further comprising an irrigation line coupled to least one of the first and second arms connecting to the first or the second jaw sections, and an aspiration line in or on at least one of the first and second arms connecting to the first or the second jaw sections.

11. The operating tool of claim 1, further comprising a structure on the second arm configured to limit movement of the pivot connection.

12. The operating tool of claim 1, wherein the first jaw section and the second jaw section remain parallel as the first jaw section linearly translates relative to the second jaw section.

13. The operating tool of claim 1, wherein the pivot connection comprises a pivot pin that connects the first arm to the second arm, and wherein automatic movement of the pivot connection comprises the pivot pin automatically moving from the first position to the second position relative to at least one of the first arm and the second arm.

\* \* \* \* \*